United States Patent [19]

O'Brien et al.

[11] Patent Number: 4,933,114

[45] Date of Patent: Jun. 12, 1990

[54] POLYACETYLENIC LIPIDS, RADIATION-SENSITIVE COMPOSITIONS, PHOTOGRAPHIC ELEMENTS AND PROCESSES RELATING TO SAME

[75] Inventors: David F. O'Brien; Thomas H. Whitesides; Richard T. Klingbiel, all of Rochester, N.Y.

[73] Assignee: Eastman Kodak Company, Rochester, N.Y.

[21] Appl. No.: 313,512

[22] Filed: Oct. 21, 1981

Related U.S. Application Data

[62] Division of Ser. No. 176,731, Aug. 11, 1980, Pat. No. 4,314,021.

[51] Int. Cl.$^5$ .............................................. C07F 9/10
[52] U.S. Cl. ................................. 260/403; 260/400; 260/404; 260/405; 260/405.5
[58] Field of Search ............... 260/403, 404, 956, 945, 260/400, 405, 405.5

[56] References Cited

U.S. PATENT DOCUMENTS

| | | | |
|---|---|---|---|
| 3,501,302 | 3/1970 | Foltz | 430/332 X |
| 3,501,308 | 3/1970 | Adelman | 430/332 |
| 3,577,446 | 5/1971 | Rakhit | 260/403 |
| 3,743,505 | 7/1973 | Bloom et al. | 560/24 X |
| 4,084,967 | 4/1978 | O'Brien | 430/202 |
| 4,229,360 | 10/1980 | Schneider et al. | 424/36 X |
| 4,348,329 | 9/1982 | Chapman | 260/403 |

OTHER PUBLICATIONS

Gupta et al, Proc. Natl. Acad. Sci. U.S.A., 74 4315 (1977).
Day, D.; Hub, H. H.; Ringsdorf, H.; *Israel Journal of Chemistry*, vol. 18 (3-4), 1979, (Pub. Apr. 1, 1980), pp. 325-329.
Chemical Abstracts, vol. 92, No. 9, Jun. 10, 1980, p. 2, Abstract No. 181708e.
Chakrabarti, P. & Khorana, H. G., *Biochemistry* 14, No. 23, Nov. 18, 1975, pp. 5021-5033.
Gupta, C. M.,; Radhakrishnan, R.; Khorana, H. G.; *Proc. Natl. Acad. Sci. U.S.A.*, vol. 74, No. 10, (Oct. 1977), pp. 4315-4319.
Cummings, Lowell, *Offic. Dig., Federation Socs. Paint Technol.* 33, 408-16 (1961).
Chemical Abstracts, vol. 89, No. 24, Dec. 11, 1978, p. 6, Abstract No. 198059e, Day, D., Stol, W. et al., "Monolayer Polymerization of Diacetylene Monocarbonic Acids at Gas-water Interface".
Chemical Abstracts, vol. 89, No. 4, Jul. 24, 1978, p. 3, Abstract No. 24875c, Day, D., Ringsdorf, H., "Polymerization of Diacetylene Carboxylic Acid Monolayers at the Gas-interface."
Hub, H. H., Hupfer B, Ringsdorf H., Division of *Organic Coating and Plastics Chemistry* vol. 42, pp. 2-7, (1980), "Polymerization of Lipid and Lysolipid Like Diacetylenes in Monolayers and Liposomes."

*Primary Examiner*—Charles F. Warren
*Attorney, Agent, or Firm*—William J. Davis

[57] ABSTRACT

A photopolymerizable monomer comprising a lipid having at least one hydrophobic acyl chain containing at least two conjugated acetylenic linkages is useful in preparing radiation-sensitive compositions and photographic elements comprising a plurality of liposomes. Further, processes for photopolymerizing the radiation-sensitive compositions and for forming an image in the photographic elements comprise exposing the lipid to radiation, heating the lipid to a temperature equal to or above a first transition temperature of the lipid to render it insensitive to further exposure, and optionally cooling the lipid to a temperature equal to or below a seocnd phase transition temperature of the lipid to render it again sensitive to further exposure. The monomeric lipids, when photopolymerized, form polymeric lipids exhibiting decreased solubility and liposome wall permeability as compared to the unpolymerized monomeric lipids.

7 Claims, No Drawings

POLYACETYLENIC LIPIDS, RADIATION-SENSITIVE COMPOSITIONS, PHOTOGRAPHIC ELEMENTS AND PROCESSES RELATING TO SAME

This is a division of application Ser. No. 176,731 filed Aug. 11, 1980 now U.S. Pat. No. 4,314,021, Feb. 2, 1982.

BACKGROUND OF THE INVENTION

1. Field of the Invention

This invention relates to photopolymerizable lipid monomers and their use in radiation-sensitive compositions, photographic elements, photopolymerization processes and processes for forming images.

2. Description of the Prior Art

Certain light-sensitive compositions comprising a lipid membrane containing a photoactivatable compound are known in the art. O'Brien, in U.S. Pat. No. 4,084,967 issued Apr. 18, 1978, discloses a photographic element comprising a binder containing numerous vesicles comprising a lipid membrane containing rhodopsin. Rhodopsin functions as a light-sensitive gate which allows diffusion of metal cations into or out of the vesicles as a function of exposure.

Further, lipid compounds which themselves contain photoactivatable groups are known. Gupta et al, Proc. Natl. Acad. Sci. U.S.A., 74 4315 (1977) disclose the synthesis of certain phospholipids having hydrophobic acyl chains containing photoactivatable groups such as trifluorodiazapropionyl, diazirinophenoxy, 2-nitro-4-azidophenoxy, m-azidophenoxy, and $\alpha,\beta$-ethylenically unsaturated keto groups, for the purpose of studying lipid-lipid and lipid-protein interactions in biological membranes. However, Gupta et al do not mention polyacetylenic groups and do not describe use of the disclosed lipids in photographic materials.

It is seen that new classes of lipids containing photoactivatable groups are desirable for use in radiation-sensitive compositions, photographic elements, and processes of forming images.

SUMMARY OF THE INVENTION

It has been found, according to the present invention, that a monomer comprising a lipid having at least one hydrophobic acyl chain containing at least two conjugated acetylenic linkages is useful in radiation-sensitive compositions, photographic elements and processes for forming images. A preferred embodiment of this invention is the use of certain phospholipid monomers having at least one hydrophobic acyl chain containing at least two conjugated acetylenic linkages. The novel monomer is colorless in the absence of absorbed radiation, but when exposed to radiation, the monomer forms a highly colored polymer having recurring units comprising a lipid having at least one hydrophobic acyl chain containing at least one pair of ethylenic linkages connecting said recurring units and having a "conjugated" acetylenic linkage between said pair of ethylenic linkages. It is understood that the above-description of the polymerized units includes all polymerized forms of the monomers, for example, resonance hybrids such as poly(1,4-substituted-1,2,3-butatriene).

Another aspect of the present invention is a radiation-sensitive composition comprising a monomeric lipid having at least one hydrophobic acyl chain containing at least two conjugated acetylenic linkages. In a preferred embodiment, the radiation-sensitive composition comprises a plurality of liposomes comprising the novel monomeric lipid. When exposed to radiation, the resulting photopolymerization changes the properties of the lipid in several ways. Exposed, polymerized liposomes are analogous to spherical bubbles with a hard shell and exhibit solubility characteristics and permeability properties different than those of unpolymerized liposomes. Further, the novel lipid liposomes are unexpectedly characterized by a temperature dependent phase transition, such that they are radiation-sensitive below the transition temperature, but not above it. This unexpected phase transition enables the storage of the novel compositions in stable insensitive form, repeated cumulative exposures interspersed with periods of insensitivity to light, and stabilization of a final image without resort to chemical processing.

In a further aspect of the invention, a process of preparing a radiation-sensitive composition having add-on exposure capability, said composition comprising a monomeric lipid having at least one hydrophobic acyl chain containing at least two conjugated acetylenic linkages, is selected from the group consisting of:

(a) (1) forming a solution of said lipid in an organic solvent, (2) evaporating said solvent to form a thin film, and (3) hydrating said thin film with an aqueous buffer solution having a pH in the range from 4 to 10; and (b) (1) forming a solution of said lipid in an organic solvent, (2) mixing said solution with an aqueous buffer solution having a pH in the range from 4 to 10 to form a dispersion of liposomes, and (3) cooling said dispersion to a temperature below a predetermined phase transition temperature.

In a further aspect of the present invention, a photographic element comprises a support having thereon a layer comprising a monomeric lipid having at least one hydrophobic acyl chain containing at least two conjugated acetylenic linkages. When imagewise exposed, the novel photographic element forms an image comprising highly colored polymeric material which is insoluble in many solvents. Thus, the photographic element is useful in the preparation of relief printing plates, lithographic printing plates and for photoresist layers. When imagewise exposed, according to the present invention, a photographic element comprises a support having thereon a layer comprising a polymeric lipid having recurring units having at least one hydrophobic acyl chain containing at least one pair of ethylenic linkages connecting said recurring units and having a conjugated acetylenic linkage between said pair of ethylenic linkages.

In a still further aspect of the present invention a process for forming an image comprises:

(a) imagewise exposing to radiation a photographic element comprising a support having thereon a layer comprising a monomeric lipid having at least one hydrophobic acyl chain containing at least two conjugated acetylenic linkages; and (b) heating said photographic element to a temperature equal to or above a first phase transition temperature of said lipid to render said photographic element insensitive to further exposure.

DETAILED DESCRIPTION OF THE INVENTION

The novel monomer comprises a lipid having at least one hydrophobic acyl chain containing at least two conjugated acetylenic linkages.

As used herein, the term "lipid" refers to amphiphatic compounds having a hydrophilic portion comprising an ionic group or a polar group, and a hydrophobic portion comprising at least one hydrophobic acyl chain, and which form bimolecular layer structures that interface with aqueous solutions. A description of lipid membranes and lipids which are useful herein is found in "Lipid Analysis" by William W. Christie, Pergamon Press, Oxford, England, 1973. Further descriptions are found in various articles such as G. B. Ansell, J. N. Hawthorne, and R. M. C. Dawson, "Form and Function of Phospholipids," Elsevier Scientific Publishing Company, Amsterdam, The Netherlands (1973); A. D. Bangham, M. W. Hill and N. G. A. Miller, "Methods in Membrane Biology" Vol. 1 ed. E. D. Korn, Plenum Press, New York (1974), page 1; S. Razin, Biochim, Biophys. Acta 265, 241 (1972); C. Tanford "The Hydrophobic Effect," Wiley-Interscience, New York (1973).

Especially useful lipids include phospholipids such as phosphatidylcholine, phosphatidylethanolamine, phosphatidylserine, phosphatidylglycerol; sphingolipids, such as sphingomyelin; glycolipids, such as cerebrosides, phytoglycolipids, and gangliosides; glycerides, such as phosphonoglycerides; glycerol ethers; dialkyl phosphates; dialkyl phosphonates; alkyl phosphinate monoalkyl esters; phosphonolipids such as ceramide-2-aminoethylphosphonic acid and phosphonglycerides; alkylammonium halides, such as N,N-disubstituted dimethylammonium halides, trialkylmethylammonium halides, and tetraalkylammonium halides; and dialkylsulfosuccinic acid esters and 2,3-diacyloxysuccinic acids.

In a preferred embodiment, the novel monomer has the formula:

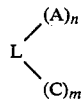

wherein:

L is the hydrophilic portion of a lipid, as described above;

A is a hydrophobic acyl chain containing at least two conjugated acetylenic linkages;

C is a saturated or unsaturated aliphatic moiety other than A;

n is an integer having a value of 1 or greater; and m is an integer having a value of 0 or greater.

In an especially preferred embodiment, the novel monomer comprises a phospholipid represented by the formula:

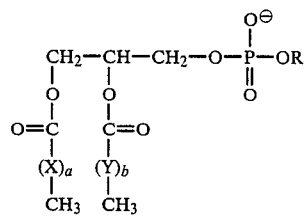

wherein:

X and Y independently are selected from the group consisting of saturated aliphatic and unsaturated aliphatic moieties, preferably containing 10 carbon atoms or greater, and more preferably from about 14 to about 38 carbon atoms, such as decylene, dodecylene, tetradecylene, hexadecylene, octadecylene, and 9-octadecenylene with the proviso that at least one of X and Y must have at least two conjugated acetylenic linkages as described below;

a and b are 0 or 1, and a+b is 1 or 2, with the proviso that when a+b is 1, the X or Y remaining must have at least two conjugated acetylenic linkages; and R is selected from the group consisting of 2-trimethylammonioethyl ($—CH_2CH_2N^{\oplus}(CH_3)_3$), ammonioethyltrimethylammonioethyl ($—CH_2CH_2N^{\oplus}H_3$), 2-carboxyammonioethyl ($—CH_2CHN^+H_3$) and 2,3-dihydroxypropyl

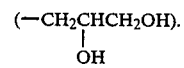

Further examples of phospholipid starting materials are found in "Methods of Membrane Biology" by Korn, Vol. 1, Plenum Press, New York 1974, pages 55 to 60.

The lipid of the invention has at least one hydrophobic acyl chain containing at least two conjugated acetylenic linkages, preferably containing 12 carbon atoms or greater and more preferably containing from about 16 to about 40 carbon atoms. Examples of such hydrophobic acyl chains include diynoyl such as 7,9-hexadecadiynoyl, 8,10-octadecadiynoyl, 9,11-eicosadecadiynoyl, 10,12-docosadiynoyl, 10,12-tricosadiynoyl, 11,13-tetracosadiynoyl, 12,14-hexacosadiynoyl, 13,15-octacosadiynoyl, 14,16-triacontadiynoyl, 15,17-dotriacontadiynoyl, 15,17-tetratriacontadiynoyl, and 16,18-hexatriacontadiynoyl; and triynoyl such as 10,12,14-pentacosatriynoyl. Further examples of hydrophobic acyl chains having conjugated acetylenic linkages are found in U.S. Pat. No. 3,743,505 issued July 3, 1973, and in Defensive Publication T910,005 published May 1, 1973.

In a preferred embodiment, the hydrophobic acyl chain has the formula:

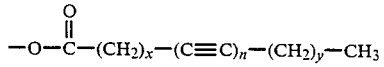

wherein n is an integer greater than 1, preferably 2, and x and y independently are integers from 1 to 12. Most preferably x is 8, y is 9 and the hydrophobic acyl chain is 10,12-tricosadiynoyl.

Examples of monomeric lipids useful in the practice of this invention include 1,2-di(tricosa-10,12-diynoyl)-sn-glycero-3-phosphorylcholine; N,N-di(tricosa-10,12- diynoyloxyethylene)-N,N-dimethylammonium chloride; bis(tricosa-10,12-diynoyl)monohydrogen phosphate; and 2,3-bis(tricosa-10,12-diynoyloxy)succinic acid.

In a preferred embodiment the novel monomer comprises a phospholipid having the formula:

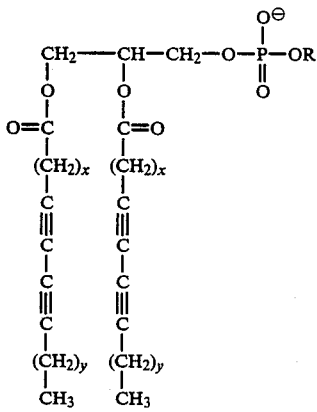

wherein:

x and y independently are integers from 1 to 12, with x most preferably being the integer 8 and y most preferably being the integer 9; and R is selected from the group consisting of 2-trimethylammonioethyl, ammonioethyl, 2-carboxyammonioethyl an 2,3-dihydroxypropyl, R preferably being 2-trimethylammonioethyl.

The monomer of the present invention is prepared by reacting an acid derivative, such as an acid anhydride or acid chloride of a hydrophobic acyl chain containing at least two conjugated acetylenic linkages, with a hydroxy-substituted derivative of the hydrophilic portion of the selected lipid molecule, or with a hydroxy-substituted derivative of the selected hydrophilic moiety also being substituted with one or more saturated aliphatic or unsaturated aliphatic moieties. A 50 to 150 percent molar excess of the acid derivative of the hydrophobic acyl chain is stirred with the appropriate hydroxy-substituted derivative in the presence of an organic solvent and an acid acceptor. Useful organic solvents include aprotic solvents such as chloroform, methylene chloride, dichloroethane, chlorobenzene and tetrahydrofuran. Useful acid acceptors include pyridine, methylpyridine, 4-dimethylaminopyridine, triethylamine and tripropylamine. Stirring takes place at room temperature under an inert atmosphere for at least one hour, preferably for about 60 hours. The resulting solution is then evaporated to dryness and the product recovered from the residue.

The anhydrides of hydrophobic acyl chains having the formula:

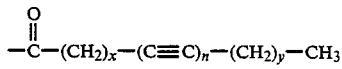

where n is 2, are prepared in accordance with the following reaction scheme:

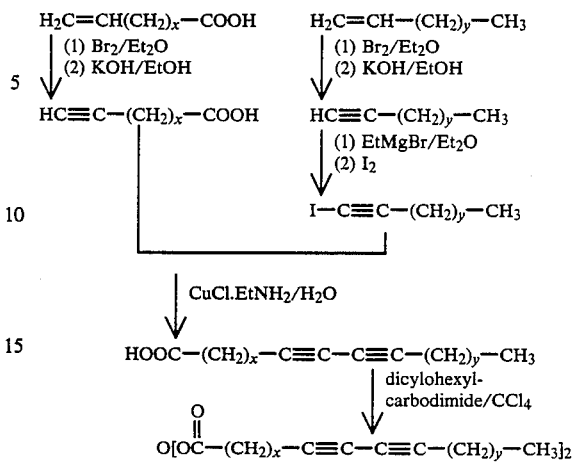

When polymerized, the novel monomer forms a polymer having recurring units comprising a lipid having at least one hydrophobic acyl chain containing at least one pair of ethylenic linkages connecting said recurring units and a conjugated acetylenic linkage between said pair of ethylenic linkages. In a preferred embodiment the novel polymer has the formula:

wherein:

B is a hydrophobic acyl chain containing at least one pair of ethylenic linkages connecting said recurring units and a conjugated acetylenic linkage between said pair of ethylenic linkages; and L, C, n and m are as previously described.

In an especially preferred embodiment, the hydrophobic acyl chain of the polymer has the formula:

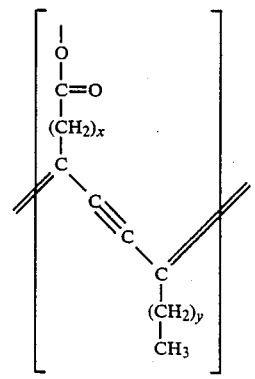

wherein x and y are as previously defined.

The polymerization proceeds as a 1,4-addition, and is topotactic, i.e. the reaction depends critically upon achieving a suitable pseudocrystalline array of monomers. Because the novel monomers tend to form bimolecular layer structures such as liposomes or vesicles, a two-dimensional array appropriate for efficient polymerization is readily formed. The polymerization is intermolecular when the novel monomer comprises a lipid having only one hydrophobic acyl chain containing conjugated acetylenic linkages. It is further believed that a novel monomer having more than one hydrophobic acyl chain containing conjugated acetylenic linkages is principally intermolecularly polymerized.

In a particularly preferred embodiment, the polymer of the invention has recurring units comprising a phospholipid having the formula:

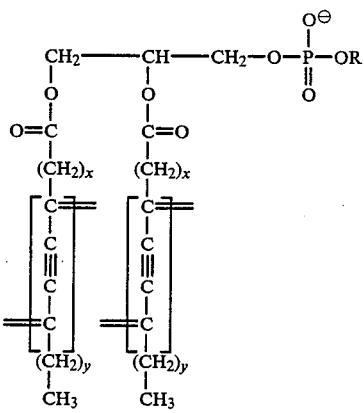

where x, y and R are as previously described.

The novel monomer is useful in preparing a radiation-sensitive composition comprising a monomeric lipid having at least one hydrophobic acyl chain containing at least two conjugated acetylenic linkages. In a preferred embodiment, the radiation-sensitive composition comprises a plurality of liposomes containing the novel monomeric lipid. As used herein, the term "liposomes" refers to spherical, closed assemblages of lipids which have at least one bimolecular layer comprising a hydrophobic portion, and a hydrophilic portion and which enclose an aqueous volume.

In one embodiment the radiation-sensitive composition comprises a hydrophilic binder. A wide variety of hydrophilic binders are useful, and the binder need not be polymeric. Preferred hydrophilic binders include gelatin, poly(vinyl alcohol), poly(N-vinyl-2-pyrrolidone), polyacrylamide and copolymers derived from acrylamide, and acrylic homo- and copolymers derived from hydrophilic monomers such as acrylic acid, methacrylic acid, vinylbenzyl alcohol, hydroxyalkyl acrylates, N-hydroxyalkylacrylamides, and sulfoalkyl acrylates. A most preferred hydrophilic binder comprises gelatin.

In another embodiment, the radiation-sensitive composition comprises a mixture of one or more of the monomeric lipids of the invention and at least one additional lipid or diluent. Examples of useful additional lipids and diluents include dioleoylphosphatidylcholine; distearoylphosphatidylcholine; cholesterol; fatty acids; phospholipids such as phosphatidylcholine, phosphatidylethanolamine, phosphatidylserine, phosphatidylglycerol; sphingolipids, such as sphingomyelin; glycolipids, such as cerebrosides, phytoglycolipids and gangliosides; glycerides, such as phosphonoglyceroides; glycerol ethers; dialkyl phosphates; dialkyl phosphonates; alkylphosphinate monoalkyl esters; phosphonolipids such as ceramide-2-aminoethylphosphonic acid and phosphonoglycerides; alkylammonium halides, such as N,N-disubstituted dimethylammonium halides, trialkylmethylammonium halides, and tetraalkylammonium halides; and dialkylsulfosuccinic acid esters and 2,3-diacyloxysuccinic acids. Preferably the additional lipid, if any, comprises dioleoylphosphatidylcholine or distearoylphosphatidylcholine.

In some embodiments, the radiation-sensitive composition comprises addenda such as coating aids, stabilizers, buffering agents or chelating agents.

In a preferred embodiment, the radiation-sensitive composition comprises a hydrophilic binder containing a plurality of vesicles, said vesicles comprising the novel monomer. "Vesicles" are a class of liposomes having a single bimolecular layer of lipids, and are commonly prepared from liposomes.

The radiation-sensitive compositions of the invention are prepared by either of two processes (a) or (b). Process (a) comprises (1) forming a solution of the lipid in an organic solvent, (2) evaporating the solvent to form a thin film, and (3) hydrating the thin film with an aqueous buffer solution having a pH in the range from about 4 to about 10. Process (b) comprises (1) forming a concentrated solution of the monomeric lipid in an organic solvent, (2) mixing said solution with an aqueous buffer solution having a pH in the range from about 4 to about 10 to form a dispersion of liposomes, and (3) cooling said dispersion to a temperature below a predetermined phase transition temperature.

Organic solvents useful in forming a solution of the monomeric lipid in process (a) include chlorinated hydrocarbons, such as chloroform, ethylene chloride, and carbon tetrachloride.

The thin film formed by evaporating the solvent in process (a) is hydrated with an aqueous buffer solution having a pH in the range from about 4 to about 10, preferably from about 4.5 to about 8.5, to form an aqueous dispersion of liposomes comprising the monomeric lipid. Useful buffering agents include N-2-hydroxyethylpiperazine-N'-2-ethanesulfonic acid (HEPES), acetate ion, phosphate ion, borate ion and imidazole. In some embodiments, the aqueous buffer solution comprises a metal chelating agent such as ethylenediaminetetraacetic acid to remove divalent cations such as $Be^{+2}$, $Mg^{+2}$, $Ca^{+2}$, $Ba^{+2}$ and $Cd^{+2}$. The ratio of the volume of the buffer solution to the amount of the monomeric lipid varies widely in the range from about 1 mL/g to about $10^4$ mL/g, but is preferably in the range from about 10 mL/g to about 150 mL/g.

Organic solvents useful in forming a solution of the monomeric lipid in process (b) include lower alkanols, such as methanol, ethanol, isopropanol, t-butanol, or methoxyethanol; ketones, such as methyl ethyl ketone, acetone, or cyclopentanone; chlorinated hydrocarbons, such as chloroform, ethylene chloride, or carbon tetrachloride; ethers, such as dioxane, diethyl ether, or tetrahydrofuran; acetonitrile; dimethyl sulfoxide; dimethylformamide; and mixtures thereof. Preferred organic solvents include ethanol and chloroform.

The concentration of the monomeric lipid in the organic solvent is dependent on the nature of the monomeric lipid and the organic solvent. However, the solutions most readily form liposomes in the aqueous buffered solution when the solution is relatively concentrated, preferably containing from about 1 to about 10 percent by weight of the monomeric lipid.

The solution of the monomeric lipid in an organic solvent formed in process (b) is mixed with an aqueous buffer solution is described above for process (a) to form an aqueous dispersion of liposomes. Methods for mixing the solution of the monomeric lipid with the aqueous buffer solution include slow injection of the lipid solution into vigorously stirred buffer solution, dropwise addition of the lipid solution into rapidly stirred buffer solution, and passage of the lipid solution over a gel permeation column which is continuously being washed with buffer solution.

Some of the dispersions of liposomes of process (b) are not originally sensitive to radiation, as are the hydrated liposomes prepared by process (a), and must further be cooled to a temperature, preferably ranging from $-10°$ to $+20°$ C. to render the dispersion sensitive to radiation. This cooling step (3) takes place before the mixing step (2) in some embodiments and after the mixing step (2) in other embodiments, but preferably occurs after the mixing step (2).

The radiation-sensitive liposomes resulting from process (a) or (b) range in size from about 250 to about 100,000 Å in diameter, as estimated by negative stain (ammonium molybdate) electron microscopy, and have wall thicknesses of about 50 Å to about 50,000 Å. In a preferred embodiment, radiation-sensitive vesicles, having a single bimolecular layer of monomeric lipids, are prepared from the radiation-sensitive compositions of process (a) or (b) by sonication with an ultrasonic probe (Bronson Model W185) at room temperature. In another preferred embodiment radiation-sensitive vesicles are prepared by treating the radiation insensitive dispersion of liposomes of process (b) with the above method and subsequently cooling the vesicles to render them sensitive to radiation. The vesicles of the invention range in size from about 250 Å to about 5000 Å in diameter, and have a wall thickness of about 50 Å.

If the radiation-sensitive composition is to comprise a hydrophilic binder, the hydrophilic binder is added to the aqueous buffer solution after process (a) or (b). Preferably, a 5 to 35 percent (weight/volume), preferably 15–25 percent, solution of the hydrophilic binder in aqueous buffer solution is mixed with the radiation-sensitive composition after completion of process (a) or process (b). The volume:volume ratio of binder solution to liposome dispersion ranges from about 0.5:1 to about 5.0:1, but preferably varies from about 2.0:1 to about 2.5:1.

The liposomes comprising the monomeric lipid of the invention are characterized by a temperature dependent phase transition associated with the conversion from a radiation-sensitive gel-like phase below the transition temperature to a radiation-insensitive liquid crystalline fluid phase above the transition temperature. When certain of the novel radiation-sensitive compositions are heated to a temperature above a first transition temperature, preferably within the range of about 30° to about 60° C., the composition is rendered insensitive to light for storage at room temperature. When cooled below a second phase transition temperature, preferably in the range from about $-10°$ to about $+20°$ C., the composition is rendered once again sensitive to radiation. Thus the radiation-sensitivity of the composition depends upon the thermal history of the lipid membranes.

Once the composition has received overall or imagewise exposure, it successively becomes insensitive to further radiation exposure upon heating above the first phase transition temperature, and then sensitive to further radiation exposure upon cooling below the second phase transition temperature, exhibiting a cumulative, "add-on" exposure capability through as many cycles as desired. When the process of cumulative exposures is complete, the composition is rendered insensitive to radiation by heating it to the first phase transition temperature, thus providing a stable image or overall density without requiring conventional processing solutions, such as fixing, bleaching or washing away unexposed material.

Although the process of photopolymerizing the radiation-sensitive composition does not appreciably affect particle size, it does change the properties of the liposomes comprising the lipid. Photopolymerized liposomes are composed of polymeric lipids insoluble in chloroform, methanol, acetone and other solvents commonly used in graphic arts processes, while unexposed, unpolymerized liposomes are soluble in these solvents. Thus, the novel radiation-sensitive composition is suitable for use in relief printing plates, for lithographic printing plates and in photoresist layers. Liposomes are analogous to spherical bubbles with flexible walls and ordinarily entrap ions and highly polar molecules in the enclosed aqueous volumes. The initial permeability properties of the walls of the liposomes, are greatly altered by polymerization. Further, polymerized liposomes, having a hard shell-like wall, exhibit decreased mobility of enzymes and membrane proteins within the walls of the liposomes, and thus enable selective control of enzyme reactions sensitive to the presence of these molecules by controlling the area or degree of exposures. Further still, the solubility of certain ions and molecules in the hydrophobic portion of the liposome bimolecular layer varies with the degree of polymerization, causing the exclusion of some previously soluble materials from the hydrophobic phase, and increasing the solubility of other materials.

In a preferred embodiment, the radiation-sensitive composition of the invention is polymerized by exposure to radiation, preferably under an inert atomosphere such as argon or nitrogen. Radiation as used herein is intended to include not only the ultraviolet, visible and infrared regions of the electromagnetic spectrum, but also electron beam radiation such as is produced by cathode ray guns, gamma rays, x-rays, beta rays, and electrical corona discharge. The various embodiments of the radiation-sensitive compositions disclosed generally are not responsive to all forms of radiation, but selectively respond to at least one or more forms of radiation. Preferably, the radiation-sensitive compositions are exposed to ultraviolet light such as, for example, that provided by high or low pressure mercury lamps or xenon lamps.

The radiation-sensitive compositions described herein are useful in a variety of photographic elements including negative-image forming elements, direct positive elements, thermally processable elements, and lithographic and photoresist elements.

The photographic elements of the invention is prepared by coating the described radiation-sensitive composition on a support. Useful coating methods include dip coating, roll coating, curtain coating, spin coating and hand doctor blade coating. Preferably, the radiation-sensitive composition is coated onto a support at a coating coverage in the range from about $10^{-3}$ to about $10^3$ grams of monomeric lipid per square meter of support, which corresponds to about $10^{15}$ to about $10^{19}$ liposomes per square meter.

Materials useful as supports for photographic elements include cellulosic products such as paper, polymers such as polyesters such as poly(ethylene terephthalate), cellulose acetate, cellulose acetate butyrate, cellulose nitrate, polycarbonates and polystyrene; metals such as aluminum, copper, zinc and tin; and siliceous materials such as glass.

The preferred methods for forming images comprise imagewise exposing the photographic element to ultraviolet light. An element which is stable to radiation is prepared by heating the element to a temperature equal to or above a first transition temperature of the monomeric lipid. Cooling the element to a temperature equal to or below a second phase transition temperature again renders the element radiation-sensitive. A further heating to a temperature equal to or above the first transition temperature once again renders the element insensitive to radiation.

The following examples are included to illustrate the practice of this invention.

EXAMPLE
1—1,2-Di(tricosa-10,12-diynoyl)-sn-glycero-3-phosphorylcholine

A monomer of the invention was prepared in accordance with the following reaction scheme:

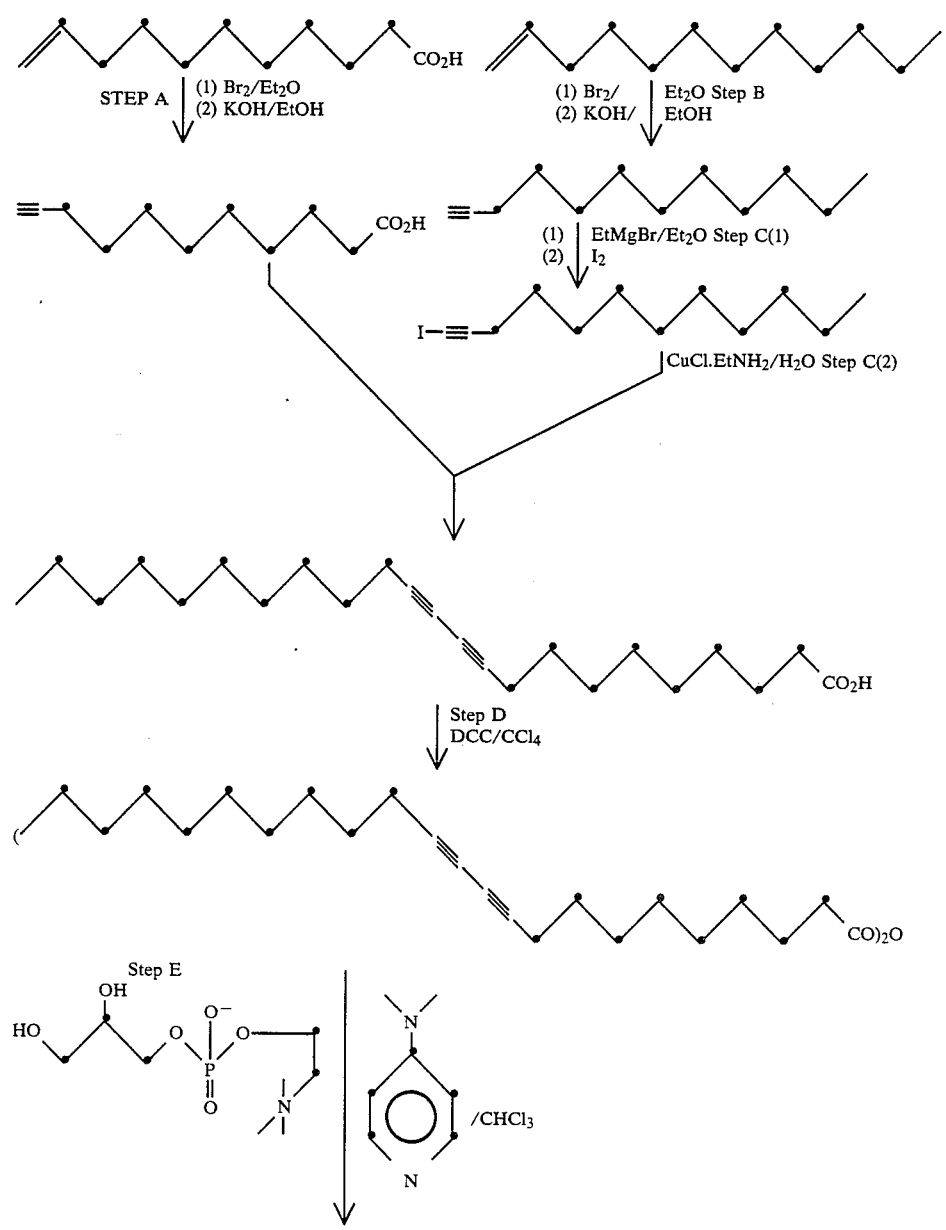

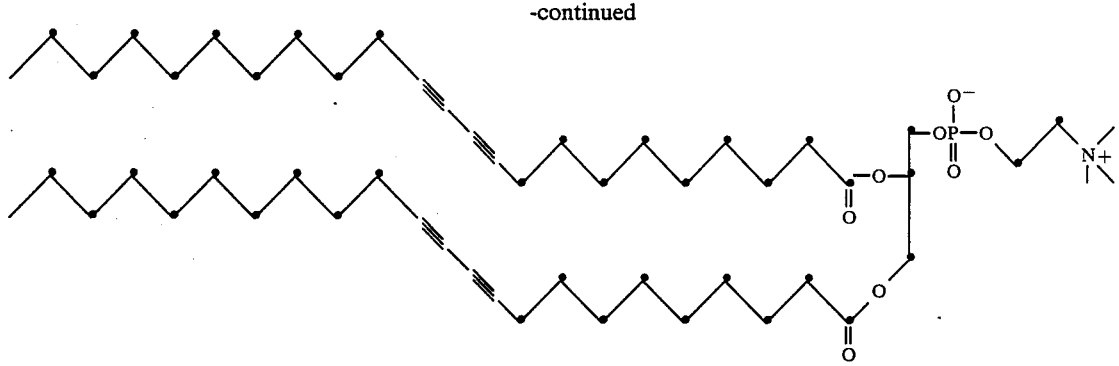

STEP A. 10-Undecynoic Acid

To 10-Undecenoic acid (100 g, 0.54 mol) dissolved in 400 mL diethyl ether was added 30 mL (93.6 g, 0.58 mol) Br$_2$ at a rate so as to maintain gentle reflux. After the addition was complete, the ether was removed under reduced pressure to yield a clear, pale yellow oil of the dibromide. This material was dissolved in 400 mL anhydrous ethanol and added to a solution of 250 g of 85 percent KOH (213 g KOH, 3.78 mol) in one L anhydrous ethanol. The heterogeneous suspension was warmed under reflux overnight, and then cooled to room temperature. The reaction mixture was neutralized to pH~1 by cautious addition of 12N HCl, and poured onto 4 L of ice. The semisolid product was extracted with ether, washed with H$_2$O and saturated aqueous sodium chloride, dried over Na$_2$SO$_4$, and the ether removed under reduced pressure. The residue was distilled under vacuum. The fraction, b.p. 120°–130°/0.6 Torr, which crystallized on standing, contained the product (59.3 g, 60%); nmr (CDCl$_3$); 1.3δ(m, 12 H, CH$_2$), 1.93 t, J=2.5 Hz, 1 H, ≡CH), 2.14 (m, 2 H, ≡CCH$_2$), 2.32 (t, J=7 Hz, 2 H, CH$_2$C=O); Ir (film) 3350 cm$^{-1}$($\nu_{V=CH}$) 2130 ($\nu_{C≡C}$), 3500–2500 (br, $\nu$ OH), 1710 ($\nu_{C=O}$).

STEP B. 1-Dodecyne

The procedure for the bromination of 1-dodecene was essentially identical to that for 10-undecenoic acid (Step A), and was carried out on a 0.54 mol scale. Dehydrohalogenation was likewise carried out as in Step A using 250 g of 85% KOH (3.78 mol) and heating under reflux for 22 hours in 1.4 L ethanol. The product was isolated by pouring the cooled reaction mixture into 3L of ice-water slush and extracting with ether. The ether layers were washed and dried as before, evaporated, and the residue distilled. The fraction bp 103–113/25 Torr contained the product (36 g, 40%), which was characterized by spectral data: nmr (CDCl$_3$) 0.9 $\tau$(m, 3 H, CH$_3$), 1.3(m, 16 H, CH$_2$), 1.91(t, J=2.5 Hz, 1H, ≡CH), 2.18 (m, 2H, ≡CCH$_2$); IR (film) 3350 ($\nu$≡CH), 2150($\nu_{C≡C}$).

STEP C. Tricosa-10,12-diynoic acid (1) 1-Iodo-1-dodecyne from 19 g (0.124 mol) ethyl bromide and 4.5 g (0.185 1 mol) magnesium turnings. 1-Dodecyne (19.9 g, 0.120 mol) and iodine (40 g, 0.157 mol) were added. After the vigorous reaction had subsided, the reaction mixture was poured into 200 mL water, acidified with acetic acid and extracted twice with ether. The organic layers were combined, washed with sodium thiosulfate solution, water, and saturated sodium chloride, dried over Na$_2$SO$_4$ and evaporated to yield an orange oil (35 g, no acetylenic CH by nmr). This material was used without purification in the next step.

(2) Tricosa-10,12-diynoic acid

10-Undecynoic acid (21.8 g, 0.120 mol) was neutralized with a solution of 57 mL 10 percent KOH in water and hydroxylamine hydrochloride (0.380 g) was added. Then a catalyst consisting of a solution of 1.9 g cuprous chloride in 16 g 70 percent aqueous ethylamine was added. A yellow precipitate formed immediately. A solution of the crude 1-iodo-1-dodecyne in 40 mL methanol was then added dropwise with stirring. The suspension was stirred for one hour after the addition. The reaction mixture was acidified by the addition of 2.5N HCl, filtered, and the filtrate and precipitate washed with ether. The ether layers were washed with water, thiosulfate solution, water and saturated sodium chloride. After drying Na$_2$SO$_4$) the solvents were removed under reduced pressure. The residue was induced to crystallize by scratching under petroleum ether. The crystals of the diyne acid (26.4 g, 74%) exhibited m.p. 57°–58° after recrystallization from acetonitrile.

STEP D. Tricosa-10,12-diynoic acid anhydride

Tricosa-10,12-diynoic acid (7.0 g, 0.02 mol) and 2.3 g (0.011 mol) dicyclohexylcarbodiimide were allowed to react in 50 mL dry carbon tetrachloride for 24 hours. The reaction mixture was filtered, the precipitate washed with ether, and the filtrate evaporated. The residue was recrystallized from ether at 0°, yield 6.45 g (95%), mp 58°–59.5°; IR (KBr) 1820, 1960 ($\nu_{CO}$), no band for OH; nmr (CDCl$_3$) 0.9 (distorted triplet, 3 H, CH$_3$), 2.28 (m, 28 H, CH$_2$), 2.22 and 2.35 (dist. t and t, 6 H, CH$_2$C≡ and CH$_2$C̄≡O, respectively).

STEP E.

1,2-Di(tricosa-10,12-diynoyl)sn-glycero-3-phosphorylchlorine (Referred to hereafter as phosphatidylcholine diacetylene)

Glycerophosphorylcholine cadmium chloride complex (0.69 g 1.5 mmol) was dehydrated by azeotropic distillation of chloroform. The dehydrated material, diynoic acid anhydride (4.0 g, 5.9 mmol, 100% excess), and 0.625 g (5.9 mmol) 4-dimethylaminopyridine were stirred in 50 mL chloroform for 60 hours under nitrogen. The resulting homogeneous solution was evaporated to dryness. The residue was taken up in 70 mL 5:4:1 methanol-methylene chloride-water, filtered, and the filtrate evaporated. The residue was redissolved in the same solvent mixture and passed through a column of Amberlyte MB-1 (Mallinckrodt) mixed bed ion exchange resin, eluting with more of the same solvent mixture. The eluant was evaporated and the eluate dehydrated by azeotropic distillation with chloroform. The residue (2.23 g) was subjected to chromatography on silica gel eluting with a methylene chloride-methanol gradient. The desired product was eluted in a broad band by pure methanol. Rechromatography on Sephadex LH-20, eluting with 1:1 $CH_2C_2$:MeOH, gave the product, a white solid, 0.8 g (58%). NMR ($CDCL_3$) 0.90$\delta$(distorted t, 6 H, $CH_3$) 1.29(m, 57 H, $CH_2$), 2.23 H (distorted t, 12 H, $CH_2\overline{CO}$ and $CH_2C\equiv$), 3.$\overline{27}$(brs, 9 H, $N+CH_3$), 3.4–4.6 ($\overline{brm}$, 9 H, $\overline{CH}_2O$ and $CH_2N+$), 5.2(brm, 1H, >C$\underline{H}$O).

EXAMPLE 2—Radiation-Sensitive Composition

A 40 mg sample of phosphatidylcholine-diacetylene prepared as described in Example 1 was dissolved in chloroform, dried to a thin film on a rotary evaporator under high vacuum. The film of lipid was hydrated with 2 mL of a buffer containing 10 mM N-(2-hydroxyethyl)-N'-(2-sulfoethyl)piperayine (HEPES), and 1 mM ethylenediamine tetraacetic acid (EDTA), pH 7.0, overnight at room temperature. The milky white aqueous dispersion of liposomes of the lipid material was flushed with argon, and a portion was irradiated in a quartz cuvette for 10 min. at a distance of 10 cm from low pressure Hg lamps (2537 Å) in a Rayonet reactor. The exposed sample changed to a deep red color with new absorption bands at 485 and 525 nm and an optical density of 0.82.

A second sample was irradiated under the same conditions for one minute. The exposed sample changed to a ( pink color with new absorption bands at 490 and 525 nm. The optical densities were 0.21 and 0.24, respectively.

A third sample was sonicated with an ultrasonic probe at room temperature under an inert atmosphere of nitrogen. The sample changed from milky white to a translucent aqueous suspension. The sample was irradiated as before for 10 min., with the resultant formation of a deep red color.

EXAMPLE 3—Phase Transition of Radiation-Sensitive Composition

A 40 mg sample of phosphatidylcholine-diacetylene was dissolved in 0.7 mL of ethanol and injected slowly (0.3 mL/min) into 50 mL of a rapidly stirred buffer solution containing 10 mM HEPES and 1 mM EDTA at pH 7.0. The buffer solution, turbid due to the formation of liposomes, was flushed with argon.

A portion of the sample was warmed to 53° C. for a few minutes, then irradiated at room temperature as in Example 1. The sample was not radiation-sensitive. A second portion of the sample was warmed to 53° C., then cooled to −10° C., then irradiated at room temperature as in Example 2, producing a suspension of red particles or liposomes.

Differential scanning calorimetry of these liposomes in aqueous buffer showed an exothermic transition of 40° C. on warming. When the same was cooled to room temperature and then reheated, the exothermic transition at 40° C. was not observed. However, when the sample was cooled to below 0° C. and then heated, the exothermic transition was once again found at 40° C.

The calorimetric data correlated with the photochemical observations. The liposomes of phosphatidylcholine-diacetylene were radiation-sensitive below the phase transition at 40° C., and were rendered insensitive when warmed to temperatures above the transition. They remained insensitive when cooled to room temperature. When further cooled to a sufficiently low temperature, however, they once again became radiation-sensitive upon returning to room temperature.

EXAMPLE 4—Mixed Radiation-Sensitive Composition

A mixed lipid system of phosphatidylcholine-diacetylene (26 mg, $2.8 \times 10^{-5}$ mol) and dioleoylphosphatidylcholine (67 mg, $8.5 \times 10^{-5}$ mol) was prepared by dissolving in chloroform, evaporating the solvent to leave a thin film of lipid, and then hydrating the lipid with buffer, 10 mM HEPES, 1 mM EDTA, pH 7.0. The white dispersion was flushed with argon. The dispersion of mixed lipid liposomes was irradiated as in Example 2 and found to be radiation-sensitive by the formation of a red color.

EXAMPLE 5—Mixed Radiation-Sensitive Composition

A mixed lipid system of phosphatidylcholine-diaceylene (26 mg, $2.8 \times 10^{-5}$ mol) and distearoylphosphatidylcholine (69 mg, $8.5 \times 10^{-5}$ mol) was prepared and irradiated as in Example 4 with similar results.

EXAMPLE 6—Radiation-Sensitive Composition Comprising Gelatin

A solution of 250 mg phosphatidylcholine-diacetylene ($2.7 \times 10^{-4}$ mol) in chloroform was dried under vacuum to give a thin lipid film. The lipid film was hydrated with 5 mL of a buffer, containing 10 mM HEPES and 1 mM EDTA at pH 7.0. The viscous white dispersion was bath- and probe-sonicated to reduce the particle size. A sample of 200 mg phosphatidylcholine-diacetylene in 4 mL buffer was diluted to 5 mL and mixed with 9 mL of a 20 percent w/v gelatin solution also containing 100 mM NaCl, 1 mM EDTA, 10 mM HEPES, buffered to pH 7.0.

A portion of the sample was maintained at room temperature and exposed to ultraviolet light as in Example 2, with the resultant formation of red polymer. A second portion was warmed to 50° C., then irradiated at room temperature. The sample was not sensitive to UV light and polymer formation was not observed.

EXAMPLE 7—Photographic Element

A mixture of 6 mL of phosphatidylcholine-diacetylene in gelatin as prepared in Example 6 was coated on subbed poly(ethylene terephthalate) support in a 0.01-inch layer at 37° C., then chill set at 18° C. for 10 min. The coating was then allowed to dry overnight to come to the humidity and temperature conditions of the laboratory.

The coating was exposed imagewise by low pressure Hg lamps (2537 Å) at a distance of 20 cm for 500 to 1000 sec. The exposed areas formed red polymer product and the unexposed areas were colorless. The color density increased with length of exposure. Multiple exposures of the same coating resulted in increased density of red polymer.

EXAMPLE 8 - 
N,N-di(tricosa-10,12-diynoyloxyethyl)-N,N-dimethylammonium chloride

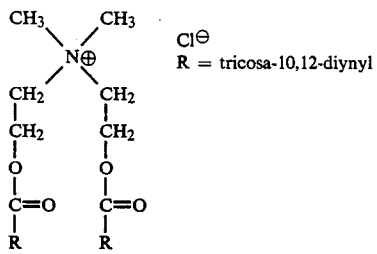

Tricosa-10,12-diynoic acid (1.72 g, 0.005 mol) and 20 mL thionyl chloride were heated under reflux for 40 minutes. The excess thionyl chloride was removed under vacuum to yield a pale yellow oil consisting of the acid chloride (IR (film) 1800 cm$^{-1}$) This material was dissolved in 15 mL $CH_2Cl_2$ and 170 mg (0.0025 mol) N,N-bis($\beta$-hydroxyethyl)-N,N-dimethylammonium chloride and 610 mg (0.005 mol) 4-(N,N-dimethylamino)pyridine were added. The reaction mixture was stirred under reflux for 6 hours. The solvent was removed under reduced pressure and the residue triturated with ether. The suspension was filtered, and the filtrate concentrated under reduced pressure. Chromatography of the residue on silica gel ($CH_2Cl_2$-methanol gradient) led to the isolation of 0.7 g (18%) of white solid, m.p. 71°-75° after recrystallization from acetone.

EXAMPLE 9—Radiation Sensitive Composition

A 40 mg sample of the N,N-di(tricosa-10,12-diynoyloxyethyl-N,N-dimethylammonium chloride prepared as described in Example 8 was dissolved in chloroform, filtered, and dried to a thin film on a rotary evaporator under high vacuum. The film was hydrated with 2 ml of a buffer as in Example 2. The milky white aqueous dispersion of liposomes of the lipid material was flushed with argon, and a portion was irradiated in a 1 mm quartz cuvette for 10 sec. at a distance of 10 cm from 6 low pressure Hg lamps (2537Å) in a Rayonet reactor. The exposed sample changed rapidly to a deep blue color with new absorption bands at 620 and 525 nm, and an optical density of 0.7.

EXAMPLE 10—Photographic Element

A sample of the ammonium salt as prepared in Example 8 was mixed with gelatin as in Example 6 and coated as in Example 7. The coating was allowed to dry overnight to come to the humidity and temperature conditions of the laboratory.

The coating was exposed imagewise with low pressure Hg lamps (2537 Å) at a distance of 10 cm for 10 to 20 sec. The exposed areas were deep blue and the unexposed areas were colorless.

EXAMPLE 11—Bis(tricosa-10,12-diynyl) Monohydrogen Phosphate

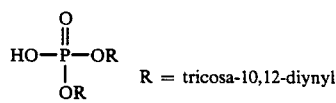

Step A. 10,12-Tricosadien-1-ol

Tricosadiynoic acid (3.44 g, 0.01 mol) in 25 mL dry tetrahydrofuran (THF) (distilled from benzophenone dianion under $N_2$) was added dropwise to a stirred suspension of 300 mg lithium aluminum hydride in 50 mL dry THF at room temperature. The addition required approximately 30 minutes. The resulting mixture was heated under reflux for 1 hour. A solution (5 ml) of $K_2CO_3$ in water (10% w/v) was added, followed by dropwise addition of 20% HCl until phase separation occurred. The organic layer was decanted, and the residue washed with ether several times. The combined organic layers were washed with water, dried over $Na_2SO_4$ and evaporated to yield 3.28 g white cyrstalline solid (99%) NMR (CDCl$_3$) δ3.60 (2H, t, $CH_2O$), 2.48 (1H, brS, OH), 2.22 (m, 4H, $CH_2C\equiv$), 1.29 (m, 30H, $CH_2$), 0.87 (3H, t, $CH_3$); IR (film) 3360, 3410 cm$^{-1}$ ($\nu$OH).

Step B. Bis(tricosa-10,12-diynyl) Monohydrogen

Phosphate (Procedure Modeled After T. Kemitake, Y. Okakata, Bull. Chem. Soc. Japan, 51, 1877 (1978)

Tricosa-10,12-diyn-1-ol (3.30 g, 0.01 mol) and 0.48 g (0.0033 mol) phosphoryl chloride were heated under reflux for 20 hours in 20 mL benzene. The reaction mixture was allowed to cool to room temperature, and the benzene removed under reduced pressure. The residue crystallized on standing. Recrystallization from hexane at 0° C. gave 0.97 g (40%) which was homogeneous by thin layer chromatography (65:25:4 methylene chloride:methanol: water; R$_f$ 0.7). An additional 0.3 g were recovered from the mother liquors by chromatography on silica gel ($CH_2Cl_2$—methanol gradient). NMR (CDCl$_3$) δ4.09 (m, 4H, $CH_2O$), 2.22 (m, 8H, $CH_2C\equiv$), 2.35 (m, 60H, $CH_2$), 0.88 (t, 6H, $CH_3$).

EXAMPLE 12—Radiation-Sensitive Composition

The bis(tricosa-10,12-diynyl)monohydrogen phosphate prepared in Example 9 was mixed with 10% $K_2CO_3$ to form a milky dispersion. On exposure to UV light (Mineralight), the dispersion became deep blue in color. ($\lambda_{max}$ 635 nm, 590(sh)). On warming, the color first changed reversibly to pink (broad maximum at 580–600 nm) and then at a higher temperature irreversibly to orange ($\lambda_{max}$ 540, 505 nm).

The invention has been described in detail with particular reference to preferred embodiments thereof, but it will be understood that variations and modifications can be effected within the spirit and scope of the invention.

What is claimed is:

1. A lipid monomer which forms bimolecular layer structures having at least one hydrophobic acyl chain containing at least two conjugated acetylenic linkages.

2. The monomer of claim 1 having the formula:

wherein:
L is the hydrophilic portion of a lipid;
A is a hydrophobic acyl chain containing at least two conjugated acetylenic linkages;

C is a saturated or unsaturated aliphatic moiety other than A;

n is an integer having a value of 1 or greater; and m is an integer having a value of 0 or greater.

3. The monomer of claim 1 wherein said lipid is selected from the group consisting of phospholipids sphingolipids, glycolipids, glycerides, glycerol ethers, dialkyl phosphates, dialkyl phosphonates, alkylphosphinate monoalkyl esters, phosphonolipids, N,N-disubstituted dimethylammonium halides, trialkylmethylammonium halides, tetraalkylammonium halides, dialkylsulfosuccinic acid esters and 2,3-diacyloxysuccinic acids.

4. The monomer of claim 1 wherein said lipid is a phospholipid represented by the formula:

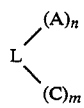

wherein:

X and Y independently are selected from the group consisting of saturated aliphatic and unsaturated aliphatic moieties with the proviso that at least one of X and Y must have at least two conjugated acetylenic linkages;

a and b are 0 or 1, and a+b is 1 or 2, with the proviso that when a+b is 1, the X or Y remaining must have at least two conjugated acetylenic linkages; and R is selected from the group consisting of 2-trimethylammonioethyl, ammonioethyl and 2-carboxyammonioethyl.

5. The monomer of claim 1 wherein said hydrophobic acyl chain has the formula:

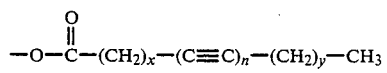

wherein:

n is 2; and x and y independently are integers from 1 to 12.

6. A phospholipid monomer which forms bimolecular layer structures having the formula:

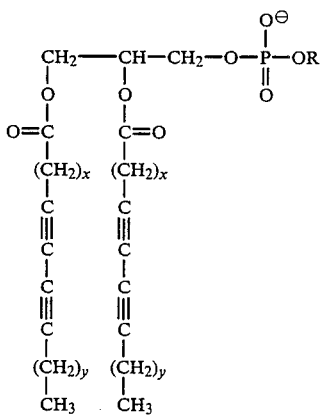

wherein:

x and y independently are integers from 1 to 12; and

R is selected from the group consisting of 2-trimethylammonioethyl, ammonioethyl and 2-carboxyammonioethyl.

7. The monomer of claim 6 wherein x is 8, y is 9, and R is 2-trimethylammonioethyl.

* * * * *